(12) United States Patent  
Fredrich et al.

(10) Patent No.: US 9,070,049 B2  
(45) Date of Patent: Jun. 30, 2015

(54) SYSTEMS AND METHODS FOR IMPROVING DIRECT NUMERICAL SIMULATION OF MATERIAL PROPERTIES FROM ROCK SAMPLES AND DETERMINING UNCERTAINTY IN THE MATERIAL PROPERTIES

(71) Applicants: Joanne Fredrich, Houston, TX (US); Elizabeth Liu, Houston, TX (US); Laurent Louis, Katy, TX (US); Dianne Ni, Katy, TX (US)

(72) Inventors: Joanne Fredrich, Houston, TX (US); Elizabeth Liu, Houston, TX (US); Laurent Louis, Katy, TX (US); Dianne Ni, Katy, TX (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 14/063,742

(22) Filed: Oct. 25, 2013

(65) Prior Publication Data

US 2014/0270394 A1 Sep. 18, 2014

Related U.S. Application Data

(63) Continuation-in-part of application No. 13/836,483, filed on Mar. 15, 2013.

(51) Int. Cl.
| | | |
|---|---|---|
| G06K 9/00 | (2006.01) | |
| G01N 15/08 | (2006.01) | |
| G01V 1/30 | (2006.01) | |
| G06T 7/40 | (2006.01) | |
| G06K 9/64 | (2006.01) | |
| G01N 24/08 | (2006.01) | |

(52) U.S. Cl.
CPC ............... *G06K 9/64* (2013.01); *G01N 15/088* (2013.01); *G01N 24/081* (2013.01); *G06T 7/40* (2013.01)

(58) Field of Classification Search
None
See application file for complete search history.

(56) References Cited

U.S. PATENT DOCUMENTS

| | | | | |
|---|---|---|---|---|
| 6,516,080 | B1 * | 2/2003 | Nur ............................... | 382/109 |
| 6,828,966 | B1 * | 12/2004 | Gavriliu et al. ............... | 345/420 |
| 8,155,377 | B2 | 4/2012 | Dvorkin et al. | |
| 2010/0198638 | A1 | 8/2010 | Deffenbaugh et al. | |
| 2011/0004447 | A1 * | 1/2011 | Hurley et al. ..................... | 703/1 |
| 2013/0262028 | A1 * | 10/2013 | De Prisco et al. ............. | 702/156 |

OTHER PUBLICATIONS

M.S. Costanza-Robinson, B.D. Estabrook, D.F. Fouhey, "Representative elementary volume estimation for porosity, moisture saturation, and air-water interfacial areas in unsaturated porous media: data quality implications." Water Resour Res, 47(7)(2011), p. W07513.*

(Continued)

*Primary Examiner* — Michael A Newman  
*Assistant Examiner* — Soo Shin  
(74) *Attorney, Agent, or Firm* — John L. Wood

(57) ABSTRACT

A testing system for analyzing a 3D digital volume of a material sample. The testing system defines several test volume sizes with each test volume size including a different numbers of voxels, defining the size of portions of the 3D digital volume to analyze. For each test volume size, the testing system acquires two adjacent portions of 3D digital volume at the test volume size currently being analyzed. The testing system calculates a material property value for the two adjacent portions of the 3D digital volume, and a difference value between the two adjacent portions of the 3D digital volume. The process is repeated over the different test volume sizes. The testing system calculates mean difference values for the different test volume sizes, from which it determines a representative elementary volume.

31 Claims, 9 Drawing Sheets

(56) References Cited

OTHER PUBLICATIONS

A.J. Hardy, "Fragment size distribution of in situ rock masses from drill core" The University of Arizona MS Thesis 1993.*

C. Müller, S. Siegsmund, and P. Blum, "Evaluation of the representative elementary volume (REV) of a fractured geothermal sandstone reservoir," Environ Earth Sci (2010) 61:1713-1724.*

T. Kanit, S. Forest, I. Galliet, V. Monoury, D. Jeulin, "Determination of the size of the representative volume element for random composites: statistical and numerical approach" Int J Solids Struct, 40 (2003), pp. 3647-3679.*

Peyman Mostaghimi, "Transport Phenomena Modelled on Pore-Space Images," PhD dissertation, Imperial College London, 2012.*

Halisch (Matthias Halisch, "The REV Challenge—Estimating Representative Elementary Volumes and Porous Rock Inhomogeneity from High Resolution Micro-CT Data Sets," 2013 Society of Core Analysts Symposium poster SCA2013-069, Sep. 16-19, 2013).*

Al-Raoush et al., Representative elementary volume analysis of porous media using X-ray computed tomography, Powder Technology, 2010, vol. 200, No. 1, pp. 69-77.

Fernandes et al., Determination of the representative elementary volume for the study of sandstones and siltstones by X-ray microtomography, Materials Research, 2012, vol. 15, No. 4, pp. 662-670.

International Search Report and Written Opinion of the ISA, PCT International Application PCT/US2014/024527 (Mar. 12, 2014).

Zhang et al., A numerical-statistical approach to determining the representative elementary volume (REV) of cement paste for measuring diffusivity, Materiales de Construcin, 2010 vol. 60, No. 300, pp. 7-20.

Constanza-Robinson et al., "Representative elementary volume estimation for porosity, moisture saturation, and air-water interfacial areas in unsaturated porous media: Data quality implications", Water Resources Research, vol. 47, No. 7 (Jul. 2011), pp. 1-12.

Li et al., "Permeability tensor and representative elementary volume of saturated cracked soil", Can. Geotech. J., vol. 46 (2009), pp. 928-942.

Kanit et al., "Determination of the size of the representative volume element for random composites: statistical and numerical approach", Int'l J. of Solids and Structures, vol. 40, No. 13-14 (2003), pp. 3647-3679.

Howarth et al., "Evaluation of Texture Features for Content-Based Image Retrieval", Image and Video Retrieval (Springer-Verlag, 2004), pp. 326-334.

International Search Report and Written Opinion of the ISA, PCT International Application PCT/US2013/032141 (Dec. 9, 2013).

U.S. Appl. No. 13/836,483, filed Mar. 15, 2013, entitled "Systems and Methods for Improving Direct Numerical Simulation of Material Properties from Rock Samples and Determining Uncertainty in the Material Properties".

* cited by examiner

SYSTEMS AND METHODS FOR IMPROVING DIRECT NUMERICAL SIMULATION OF MATERIAL PROPERTIES FROM ROCK SAMPLES AND DETERMINING UNCERTAINTY IN THE MATERIAL PROPERTIES

CROSS-REFERENCE TO RELATED APPLICATIONS

This application is a continuation-in-part of copending application Ser. No. 13/836,483, filed 15 Mar. 2013, incorporated herein by this reference.

STATEMENT REGARDING FEDERALLY SPONSORED RESEARCH OR DEVELOPMENT

Not applicable.

BACKGROUND OF THE INVENTION

This disclosure relates generally to methods and systems for analyzing three dimensional digital volumes of material samples to determine properties of the sampled material.

Knowledge of the material properties, also referred to as physical or petrophysical properties, of subsurface rock formations is important for assessing hydrocarbon reservoirs in the earth, and for formulating a development strategy regarding those reservoirs. Traditionally, samples of the rock formation of interest are subjected to physical laboratory tests to determine these material properties. These tests, however, are typically time consuming and expensive. Hence, there is a desire to develop technologies that can obtain reliable estimates of material properties of the subsurface rock, at a fraction of the time and cost of traditional laboratory based approaches.

Direct numerical simulation of material properties from digital images of rock is one promising technology aimed at achieving this objective. To determine the material properties utilizing this approach, an x-ray tomographic image is taken of a rock sample, and a computational experiment is applied on the digital image volume to simulate a specific physical experiment. Material properties such as porosity, absolute permeability, relative permeability, formation factor, elastic moduli, and the like can be determined using this conventional approach.

Direct numerical simulation has the potential to provide material properties of difficult rock types, such as tight gas sands or carbonates, within a timeframe that is substantially shorter than that required for experimentally derived material properties. This is because the process for achieving the physical conditions necessary for a specific experiment, such as full water saturation, to proceed can be quite slow. In contrast, the analogous numerical conditions that replicate the physical experiment are readily and rapidly achievable.

For most rock types, it is necessary to acquire high resolution images of the rock to resolve its pore space. This usually requires the images to be taken on a small rock sample, for example a sample extracted from a larger rock sample such as a plug, rotary core or whole core. However, pore system heterogeneity may not always be well-represented within such a small imaged portion of the rock. In some cases, the computational domain is too small for the pore system and the computed material properties fluctuate significantly about the true value for the rock.

This issue is often ignored in conventional direct numerical simulation of material properties from experimentally acquired images. Rather, computations are performed on the largest possible volume extractable from the image, without regard to whether the computational domain is appropriate for the pore system. Thus, the computed material properties may be in error due to lack of pore system representativeness.

To establish whether computed material properties are impacted by a lack of pore system representativeness, Representative Elementary Volume (REV) analysis is sometimes performed. This approach is quantitative, in that if a representative elementary volume is shown to exist, its size is also determined. By conducting this analysis, the effect of pore scale variability and scale dependence on material properties can be directly assessed.

Traditionally, the REV has been defined as the volumetric extent of a rock from which computational experiments or physical measurements will return values that are representative of the larger, or macroscopic, homogeneous rock mass. That is, the REV is defined as the sample volume size at which the physical parameter being computed or measured from the sample volume is not dependent on the particular location of the sample volume within the overall mass. Conversely, the data from computational measurements or experiments made on a computational domain or rock sample of a volume smaller than the REV may not accurately represent the pore system of the rock mass macroscopically, but the physical parameter being computed or measured will vary depending on the location of the computational domain within the rock mass. As the size of the sample volume approaches that of the REV, the computed or measured parameter will tend toward a true representative value. Computations and experiments performed on volume sizes greater than the representative volume will return values equivalent to those obtained on the volume defined as the REV (i.e., the representative value), provided that no macroscale heterogeneities are present.

FIG. 1 illustrates the traditional definition of the REV for porosity of a porous medium. In FIG. 1, the sample volume is denoted by $\Delta V_i$, the REV volume is denoted by $\Delta V_0$, and $n_i$ represents the void space volume divided by the volume of the sample. In sampling volumes $\Delta V_i < \Delta V_0$, only a small number of pores and grains are present. This situation is shown in the left-hand pane of FIG. 2, in which sample volumes $\Delta V_i$ are smaller than the REV $\Delta V_0$, and do not include a sufficient number of pores and grains to permit a physically meaningful statistical average of porosity to be determined. As a result, the porosity calculation over these sample volumes will tend to reflect local pore scale variability rather than accurately represent the porosity of the overall porous medium. As the sample volume size decreases further below the REV, the calculated ratio of void space to total volume will approach one or zero, depending on whether the centroid P of the sample volume happens to be situated within a pore or a grain. In that case, the value of $n_i$ is dominated by local micro scale variability of the pore space.

On the other hand, sample volumes $\Delta V_i$ of a size at or above the REV $\Delta V_0$ contain a sufficient number of pores and grains to permit a physically meaningful statistical average of the overall rock to be determined from a sample. This is shown in the right-hand pane of FIG. 2, in which sampling volumes $\Delta V_i$ are greater than the REV $\Delta V_0$, such that porosity calculation for volume will reflect the actual porosity value of the porous medium (i.e., the relative pore space $n_i = \phi$). For sample volumes $\Delta V_i \gg \Delta V_0$ of a homogenous porous medium, the calculated or measured porosity is essentially constant at the same porosity as represented at the REV sample volume size. However, for an inhomogeneous porous medium, macroscale inhomogeneities will cause fluctuations in the porosity, even over a population of sample volumes $\Delta V_i \gg \Delta V_0$.

This classical definition of the REV underpins the continuum framework for definition of material properties of porous materials. That is, porosity, permeability, formation factor, etc. are all defined as volumetric averages of microscopic properties at the REV volume. However, an REV for one material property, such as porosity, may not necessarily be the REV for another material property, such as permeability.

BRIEF SUMMARY OF THE INVENTION

Embodiments of this invention are directed to a method and system for analyzing material samples to determine material properties from a three-dimensional (3D) digital volume of a material sample. A plurality of test volume sizes are defined, each test volume size having a number of voxels differing from the others. A difference value in a material property for two adjacent sample volumes in the 3D digital volume, at each of the plurality of test volume sizes, is determined. A representative elementary volume for testing the material sample is then identified from the set of difference values taken over the plurality of test volume sizes.

BRIEF DESCRIPTION OF THE SEVERAL VIEWS OF THE DRAWING

Various features of the described embodiments can be more fully appreciated, as the same become better understood with reference to the following detailed description of those embodiments when considered in connection with the accompanying figures, in which.

DETAILED DESCRIPTION OF THE INVENTION

For simplicity and for illustrative purposes, the principles of this invention will be described with reference to various embodiments. However, one of ordinary skill in the art would readily recognize that the same principles are equally applicable to, and can be implemented in, all types of information and systems, and that any such variations do not depart from the true spirit and scope of this invention. Moreover, in the following detailed description, references are made to the accompanying figures, which illustrate specific examples of various embodiments and implementations. Electrical, mechanical, logical and structural changes can be made to the examples of the various implementations without departing from the spirit and scope of this invention. The following detailed description is therefore not to be taken in a limiting sense relative to the scope of this invention as defined by the appended claims and their equivalents.

Embodiments of this invention relate to systems and methods for enabling and enhancing the direct numerical simulation of material properties from digital volumes. For purposes of this description, digital volumes useful in connection with embodiments of this invention include, but are not limited to, image volumes acquired from porous material, derivative volumes obtained from such image volumes, and constructed volumes. For example, a three dimensional (3D) image volume can be acquired utilizing experimental techniques such as x-ray tomography (including micro x-ray tomography and nano x-ray tomography), Focused Ion Beam Scanning Electron Microscopy, Nuclear Magnetic Resonance and Neutron tomography. Derivative volumes can be obtained by applying segmentation processes or other image processing methods on these and other image volumes. Constructed volumes refer to image volumes that are generated using numerical processes, statistically derived, geologically modeled, or resulting from data mining or machine learning.

Each digital volume is typically represented by regular 3D volume elements referred to in the art as "voxels". Generally, each voxel is cubic, having sides of equal length in the x, y, and z directions. The digital volume itself can contain different numbers of voxels in the x, y and z directions. Each voxel within a digital volume has an associated numeric value, or amplitude, that represents the relative material properties of the imaged sample at that location of the medium represented by the digital volume. The range of these numeric values, commonly known as the grayscale range, depends on the type of digital volume, the granularity of the values (e.g., 8 bit or 16 bit values), and the like. For example, the voxels of a typical x-ray tomographic image volume represented by 16 bit data values can have amplitudes ranging from 0 to 63535.

Figure 1:
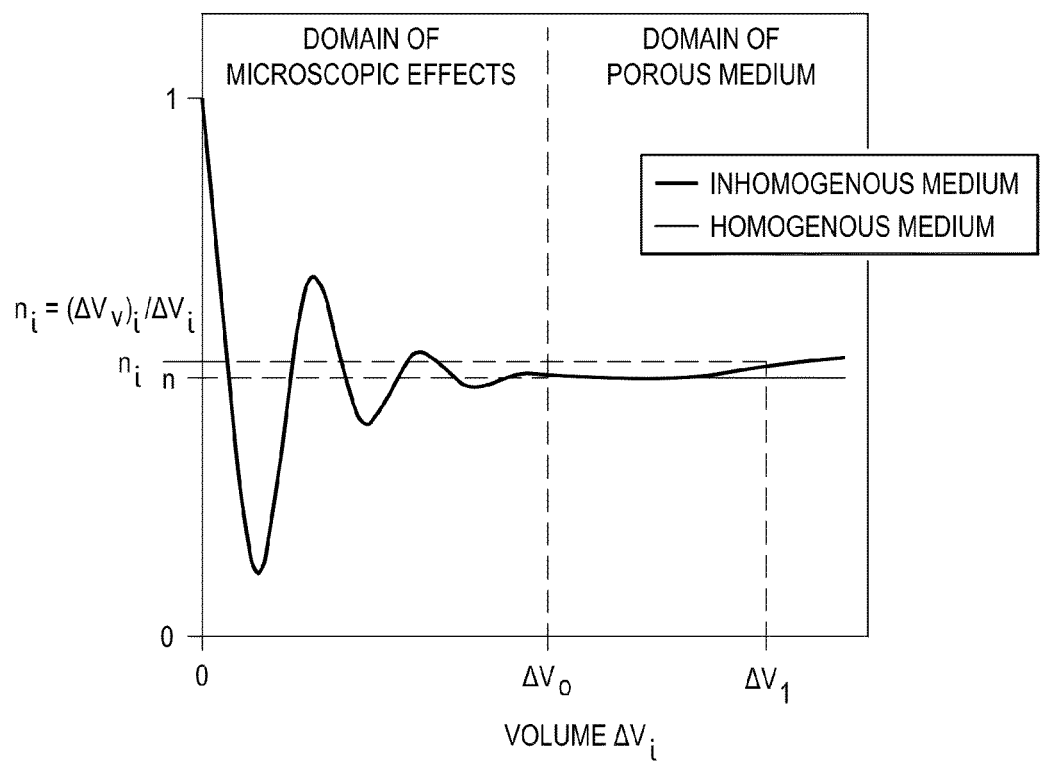
FIG. 1 is a diagram that illustrates a traditional definition of the REV for porosity for a porous medium.
Figure 2:
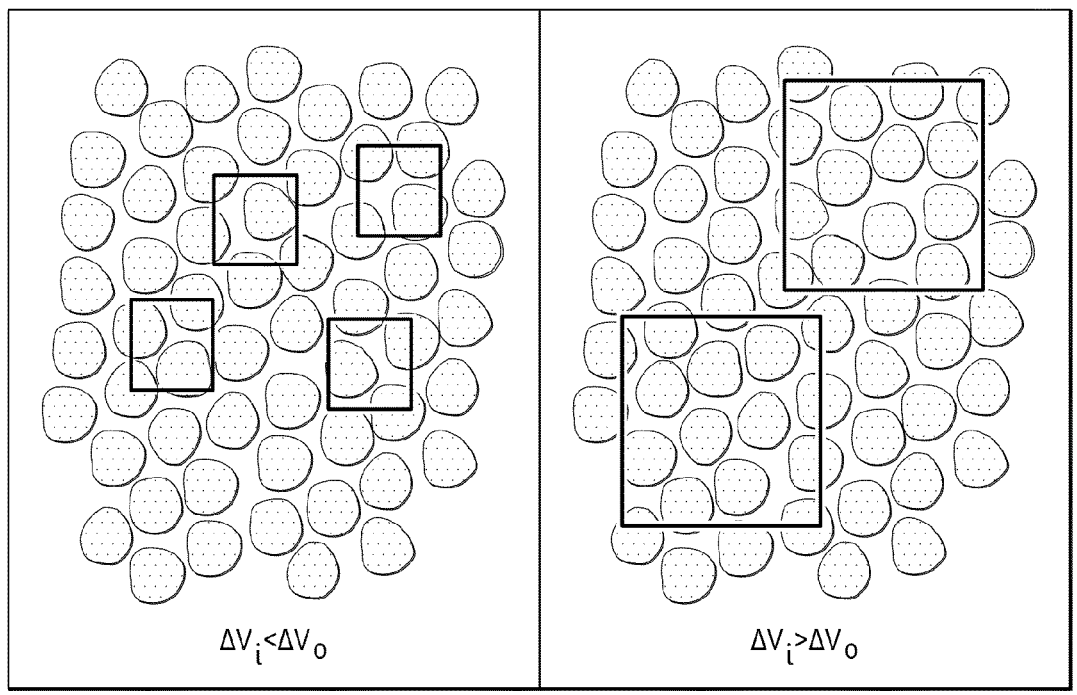
FIG. 2 is a diagram that illustrates examples of sample volumes.
Figure 3:
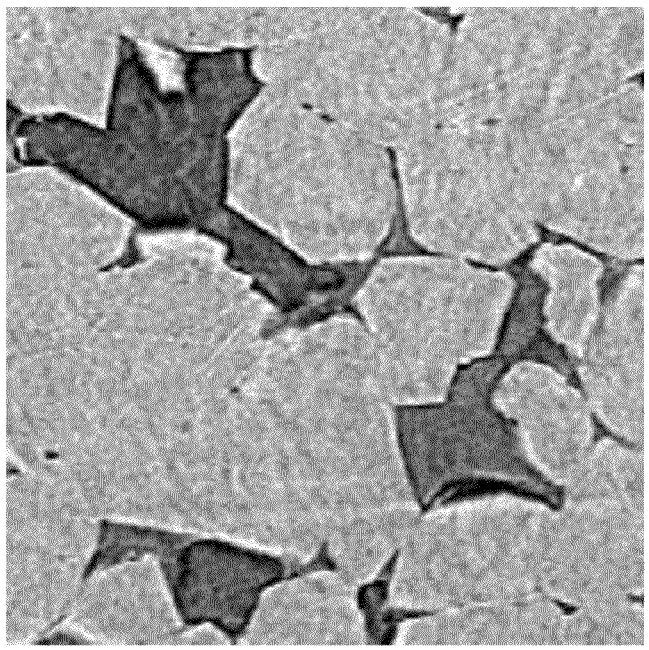
FIG. 3 is a diagram that illustrates an example of an x-ray tomographic image acquired from a sandstone rock sample under ambient pressure and dry fluid saturation, according to embodiments of the invention.

As described herein, relative material properties mean the material properties of the sample at a specific location relative to the material properties of other locations of the sample. For acquisition systems utilizing x-rays, these relative material properties effectively measure the relative density at locations of the sample. FIG. 3 illustrates one example of an input type for the process described below, as useful in connection with embodiments of this invention. In particular, FIG. 3 illustrates an x-ray tomographic image acquired from a sandstone rock sample under ambient pressure and dry fluid saturation. This image volume shows a range of grayscale values representing the intensity of the x-ray absorption within the sample. The variation in the grayscale data values exhibit differences in the amount of x-ray absorption, which generally correlate to differences in material density within that rock sample.

In derivative volumes, voxels may have their original amplitude value modified, for example by image processing routines such as artifact reduction or noise filtering, to minimize artifacts and noise generated during acquisition. Usually, this form of image enhancement is applied as part of image acquisition, but may instead or also be applied after acquisition to improve the quality of the acquired image data. Another type of image processing used to generate a derivative volume is referred to as segmentation, in which the amplitude of each voxel is assigned to one of a restricted set of numeric values. Segmentation is generally useful for performing feature identification, and can be performed by way of an automated numerical process, or by hand-picking values. Either approach involves assessing the characteristics of an image, derivative, or constructed volume, for example the characteristics of voxel amplitude, voxel amplitude connectivity or disconnectedness, or shape of connected or disconnected amplitude bodies.

One example of a segmentation process is referred to in the art as thresholding. In this context, thresholding is commonly utilized to separate pore space from grain space within an image volume. A threshold value is chosen within the voxel amplitude range, such that voxels having amplitudes below this threshold value are quantized to a specific numeric value denoting pore space, while voxels having amplitudes above that threshold are quantized to another numeric value denoting grain space. In this instance, thresholding will convert a grayscale image volume to a derivative volume in which each voxel has one of two possible numeric values, commonly 0 and 1. Thresholding can be applied any number of times, or using any number of different threshold values, to denote various features within a grayscale image.

Another example of a segmentation process is referred to as "Otsu's method". Otsu's method uses a histogram-based thresholding technique, where the threshold is chosen to minimize the variance between lobes of a bimodal distribution of grayscale values. Otsu's method can be automated, and can also be extended by repeating its segmentation of a digital volume multiple times. Other examples of automated segmentation algorithms of varying complexity known in the art, such as Indicator Kriging, Converging Active Contours, Watershedding, and the like, can instead or also be utilized to distinguish different features of an image volume.

Figure 4:
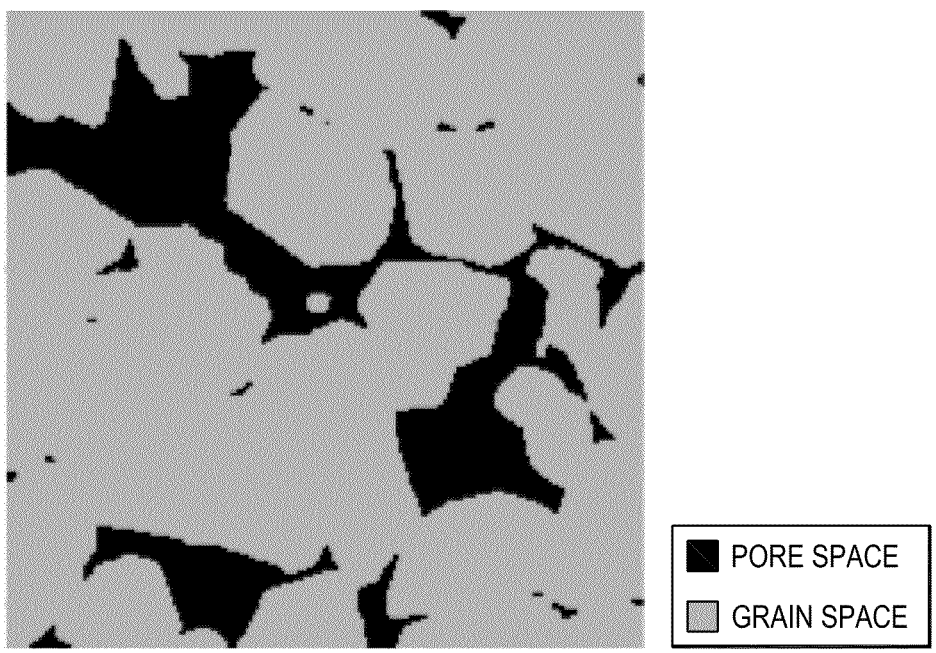
FIG. 4 is a diagram that illustrates an example of an application of a simple segmentation algorithm to the x-ray tomographic image of FIG. 3, as useful in connection with embodiments of the invention.

FIG. 4 illustrates an example of an application of a simple thresholding segmentation algorithm to the x-ray tomographic image of FIG. 3, according to various embodiments of this invention. As illustrated in FIG. 4, the segmentation algorithm has been utilized to convert a grayscale microtomographic image into a derivative volume. The black colored portions of the volume are labeled as pore space. The gray portions of the volume are labeled as grain space.

Figure 5:
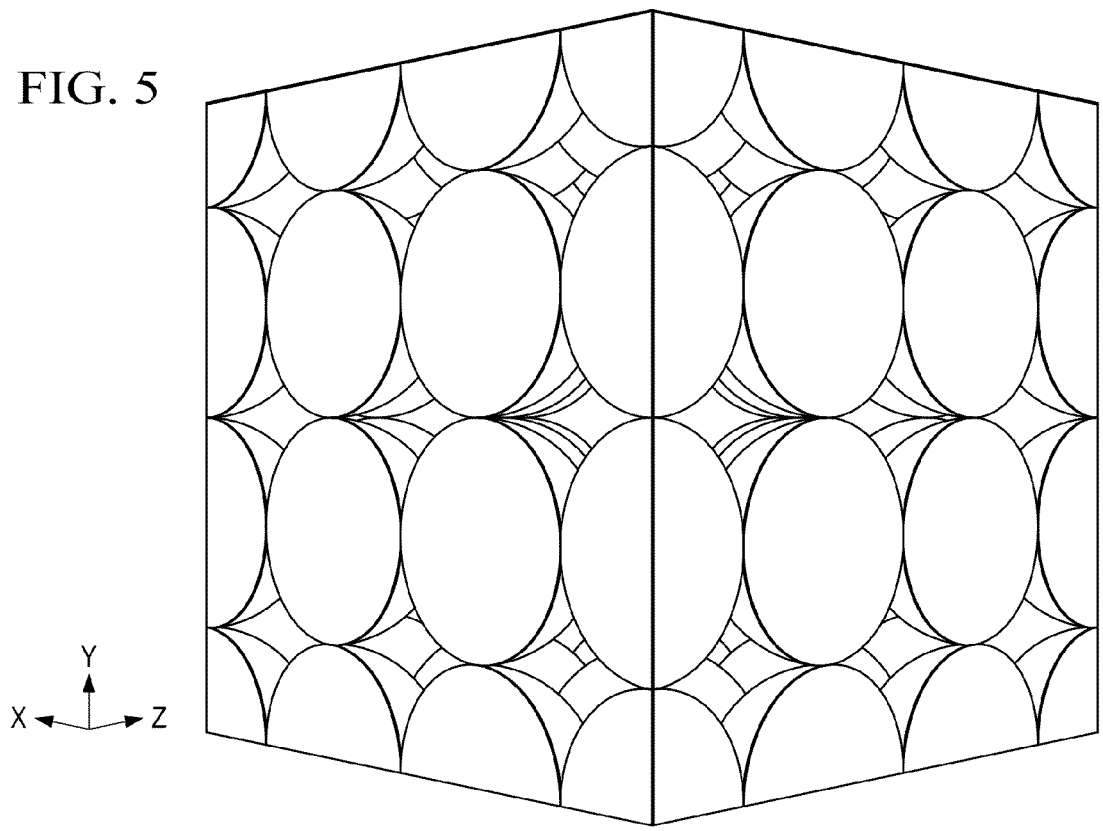
FIG. 5 is a diagram that illustrates an example of a constructed volume generated by a cubic packing of spheres, as useful in connection with embodiments of the invention.

Constructed volumes refer to digital volumes that are computer-generated, typically algorithmically or from simulation methods, rather than based on digitization of an image of an actual rock sample. The numerical algorithms used to generate constructed volumes can vary in complexity, including replicating granular and porous material simply by generating a cubic packing of spheres, or randomly inserting spheres into a cubic volume, or by way of more complex approaches of mimicking depositional and compaction processes. Geostatistical routines may be utilized to generate constructed volumes as random binary media according to correlation functions and the like. Generally, constructed volumes do not require subsequent segmentation to identify different features of the digital volume, as sufficient algorithmic labeling is usually inherent in the construction. However, in some circumstances it may be necessary to perform subsequent segmentation to identify additional features within the constructed digital volume. FIG. 5 illustrates an example of a constructed volume generated by a cubic packing of spheres, with the packing generated by numerically inserting spheres of uniform radius into a three dimensional cubic lattice.

According to embodiments of this invention, a testing tool analyzes 3D digital volumes of types including 3D digital image volumes, derivative volumes, and constructed volumes. For the case of 3D digital image volumes, these volumes may be images of rock samples obtained from whole core, side wall cores, outcrops, drill cuttings, and laboratory generated synthetic rock samples, such as sand packs and cemented packs, obtained from rock samples under ambient pressure conditions or under confining stress, from samples having some level of fluid saturation, or from samples under an assortment of other experimental conditions. Additionally, the testing tool can perform the processes described herein on 3D digital volumes of other porous materials, such as paper, bone, etc.

An example of a testing tool suitable for carrying out the functions and processes described in this specification will be described in further detail below in connection with computing device 1200 shown in FIG. 12. In any case, the testing tool may be implemented as software, hardware, or a combination of both software and hardware, in any case including the necessary logic, instructions, routines, and algorithms to perform the functionality and processes described herein. For example, the testing tool can be implemented as a standalone application program, or can be a program module that is part of another application or program.

Figure 6A:
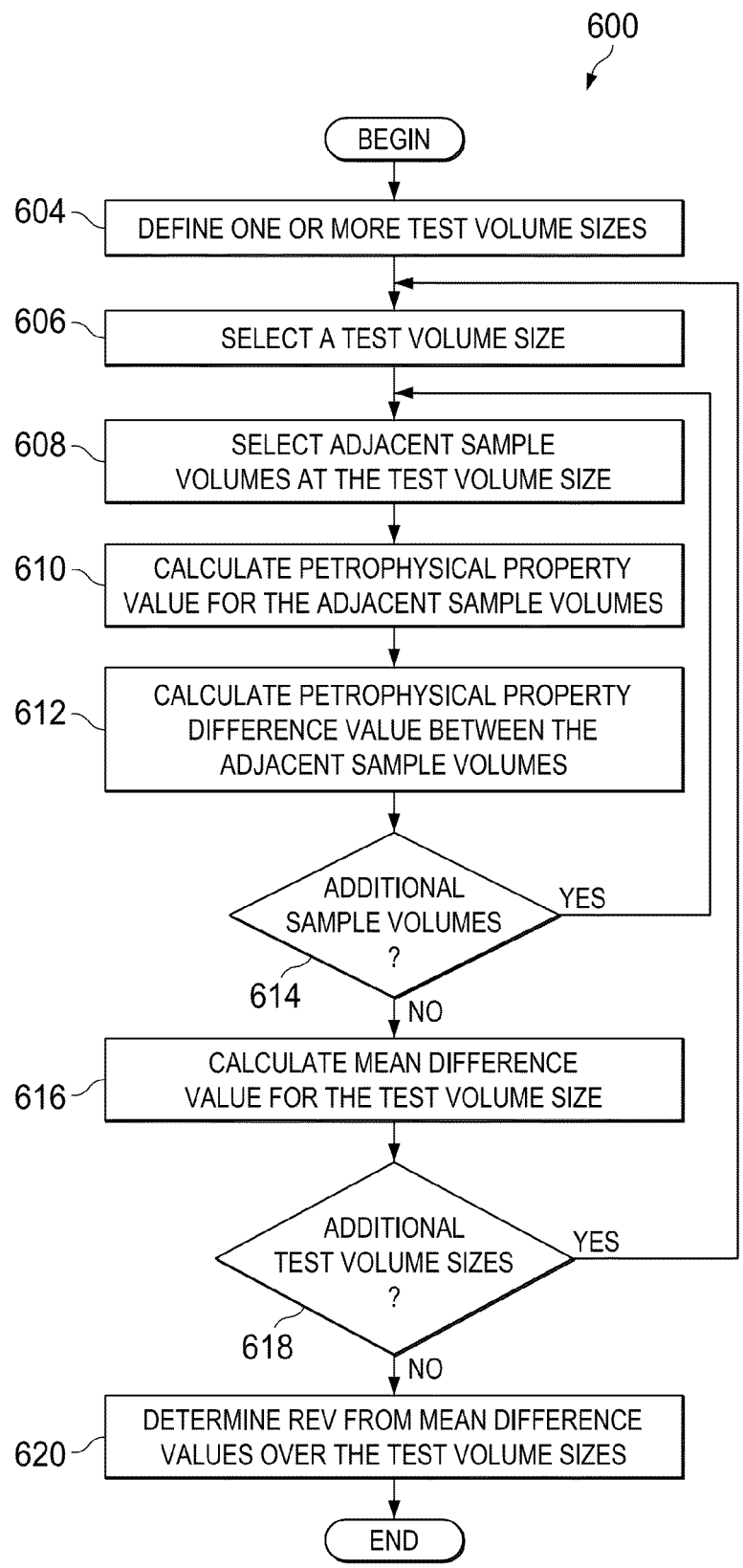
FIGS. 6a and 6b are flow diagrams illustrating examples of a process utilized to analyze 3D digital volumes, according to embodiments of the invention.

FIG. 6a illustrates an example of process 600 for analyzing a 3D digital volume, according to an embodiment of the invention. It is contemplated that variations of this process 600 will be apparent to those skilled in the art having reference to this specification, such variations including the removing of processes, including additional process stages, or altering the order in which the illustrated stages are performed.

In process 604, the testing tool defines a set of test volume sizes, each test volume size corresponding to a unique number of voxels among the set of test volume sizes. According to this embodiment of the invention, for each of the set of test volume sizes, the testing tool will analyze one or more pairs of adjacent portions of the 3D digital volume having that test volume size. As such, in process 606, the testing tool selects one of the test volume sizes for analysis. In process 608, the testing tool acquires, from the 3D digital volume, a pair of sample volumes of a size equal to the selected test volume size, and located adjacent to one another in the 3D digital volume.

In process 610, the testing tool calculates one or more material properties for each of the adjacent sample volumes selected in process 608, using direct numerical simulation or other numerical or synthetic methods. In embodiments of the invention, these material properties are physical properties of the material of the porous medium that is represented by the 3D digital volume. These material properties that may be calculated in process 610 include physical properties of any one or more of various types including porosity, permeability, relative permeability, electrical properties, elastic properties, geometrical properties, nuclear magnetic resonance (NMR), and the like. Electrical properties that may be calculated in process 610 include such properties as formation factor, resistivity index, tortuosity factor, cementation exponent, and saturation exponent. Elastic properties that may be calculated in process 610 include such properties as bulk modulus, shear modulus, Young's modulus, Poisson's ratio, compressional wave velocity, and shear wave velocity. Other material properties that may be calculated in process 610 include correlation lengths, surface to volume ratio, tortuosity, chord lengths, pore throat radii, pore size, pore shape, grain size, and grain shape, and the like. For example, porosity can be obtained for a segmented derivative sample volume by dividing the total number of pore space voxels by the total number of voxels contained within the sample volume. Absolute permeability can be computed by using a variety of numerical methods such as finite element, finite difference or lattice Boltzmann (LB) methods. These numerical approaches can simulate the physics of single phase fluid flow to compute permeability by either directly solving/approximating the Navier-Stokes equations or recovering the Navier-Stokes equation from a discretization of the Boltzmann equation. Geometrical properties, such as correlation lengths, chord lengths, etc. can be obtained using Monte Carlo-like methods, where certain characteristics are randomly sampled throughout each adjacent sample volume. For instance, the correlation length can be estimated by randomly sampling two points displaced at a given distance. In any case, process 610 calculates one or more of these material properties for each of the adjacent sample volumes selected in process 608.

In process 612, the testing tool then calculates a difference value between the material property values computed in process 610 for the adjacent sample volumes of the 3D digital volume. For example, this difference value may represent the percentage or fractional difference in the material property values between those two adjacent portions of the image volume, at the current test volume size. Decision 614 determines whether additional one or pairs of sample volumes are to be selected and analyzed. For example, decision 614 in this implementation can be based on the value of a counter that determines whether a pre-selected number of sample volume pairs to be analyzed for the current test volume size has been completed. If so (decision 614 is "yes"), the process is repeated with the selection of another pair of adjacent test volumes at the current test volume size, in process 608, followed by the calculations of processes 610, 612 to determine a difference value for that new pair.

If the desired number of sample volume pairs has been analyzed for the current test volume size (decision 614 is "no"), the testing tool then calculates the mean of the difference values obtained over for the set of adjacent sample volumes at the current test volume size, in process 616. One or more other statistics that reflect the variance of the material property values between adjacent pairs of sample volumes at this current test volume size may alternatively or additionally be calculated from these results. This mean difference value (or such other statistics) over the set of pairs of adjacent sample volumes at this test volume size can be used to determine a difference value that is representative of the current specific test volume size.

Figure 6B:
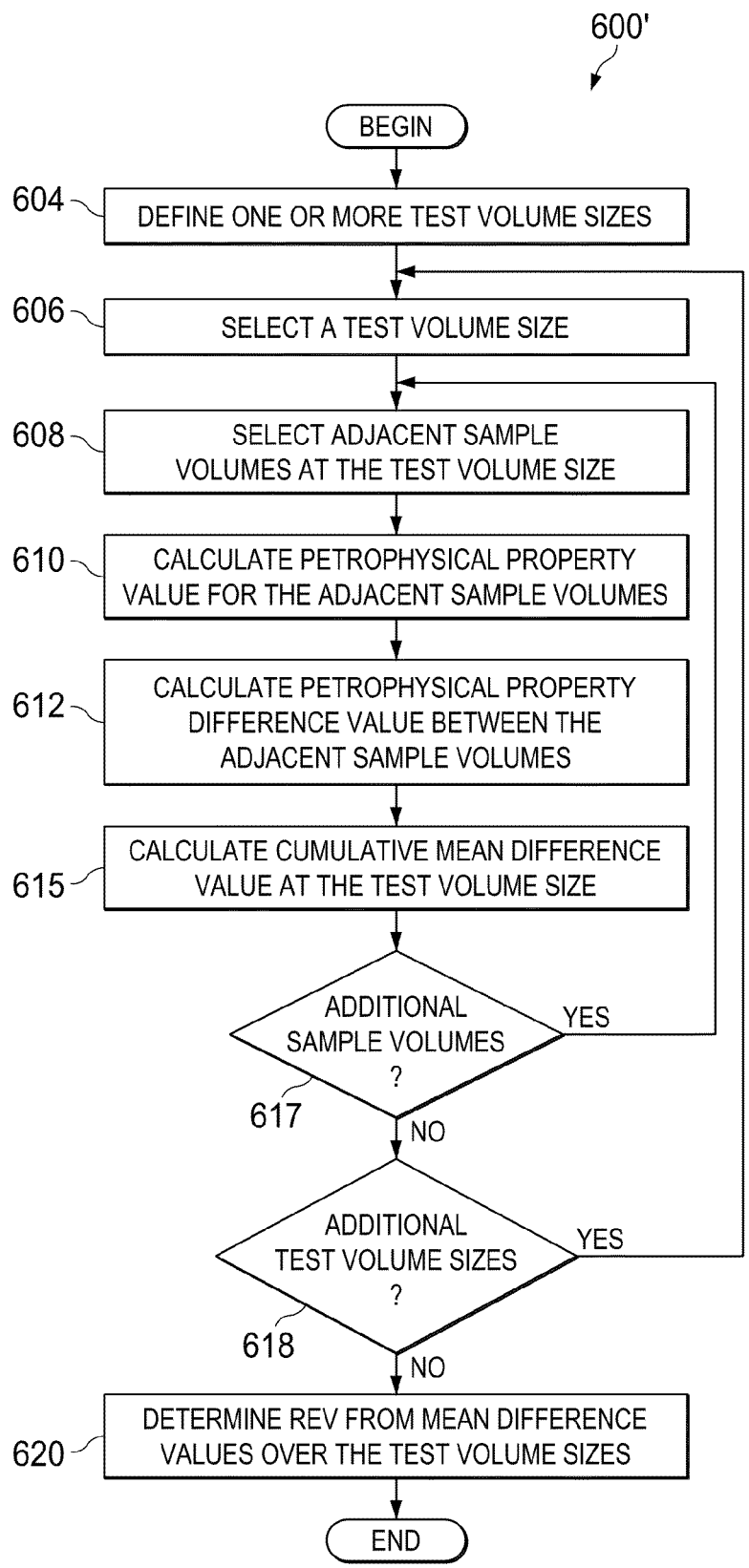

FIG. 6b illustrates an alternative approach to evaluating adjacent sample volumes for a given test volume size, according to embodiments of this invention. In this alternative implementation, processes 604 through 612 are carried out by the testing tool as described above in connection with the implementation of FIG. 6a. Following each instance of the calculating of one or more material properties for each pair of adjacent sample volumes in process 612, however, the testing tool calculates a cumulative mean difference value at the current test volume size for the sample volume pairs analyzed so far for the current test volume size, in process 615. This cumulative mean difference value for the current test volume size provides a measure of convergence that is useful in executing decision 617 to determine whether additional sample volumes at the current test volume size ought to be selected for analysis. Convergence may be based on whether the calculated cumulative mean difference value changed after the most recent instance of process 615, or on some other measure or statistic derived from this cumulative mean difference value. If convergence has not yet been reached (decision 617 is "yes"), another pair of adjacent sample volumes is selected at the current test volume size in process 608, and processes 610 through 615 are repeated for the new pair.

Figure 7:
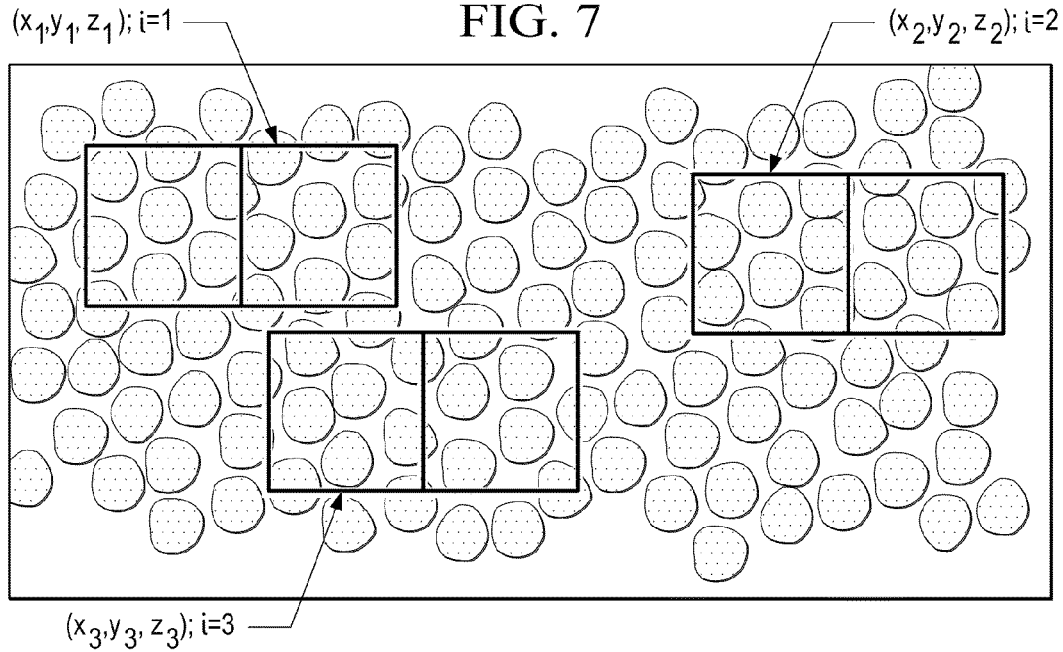
FIG. 7 is a diagram that illustrates an example of sampling strategy, according to embodiments of the invention.

In either case (i.e., according to either of the approaches of FIGS. 6a and 6b), the selection of the next pair of adjacent sample volumes in process 608 following a "yes" result from decision 614 or 617 can be carried out according to any of a number of techniques. More specifically, the locations of the two adjacent sample volume pairs within the 3D digital volume can be selected randomly, systematically, or according to a stratified strategy provided that both adjacent sample volumes in a pair lie within the entire 3D digital volume. The choice of sampling strategy depends on the heterogeneity or homogeneity of the pore structure. For instance, if the pore structure appears homogeneous on a scale much smaller than the initial test volume size, then a systematic sampling strategy can provide a more efficient method to sample the 3D digital volume than straight random sampling. That is, two adjacent sample volumes may be selected at a sampling interval specified by a fixed number of voxels from the previous two adjacent sample volumes, where the first two adjacent sample volumes of the series are chosen at a random location within the 3D volume. FIG. 7 illustrates an example of a sampling strategy in which the testing tool utilizes random sampling. In this example, three different adjacent test volumes have been selected to sample the 3D volume. The squares represent cubic volume sampling the porous medium at random spatial locations given by $(x_i, y_i, z_i)$ where $i=1:n$.

Upon the testing tool determining that no additional sample volume pairs are to be selected and analyzed (i.e., decision 614 is "no" and process 616 is completed according to the approach of FIG. 6a, or decision 617 is "no" according to the approach of FIG. 6b), the testing tool determines whether this process is to be repeated for additional sample volume sizes in decision 618. Decision 618 may be carried out in various ways. For example, the process may be performed on a predetermined set of test volume sizes, in which case decision 618 will simply determine whether that set has been exhausted. Alternatively, the testing tool may analyze the mean difference values for the test volume sizes processed so far, for example by analyzing a plot or statistical representation of those mean difference values to determine whether a representative elementary volume (REV) that meets a pre-defined difference value or variance has yet been identified. Likewise, a plot of the mean difference values can be utilized to determine the uncertainty in material properties that have been calculated or numerically simulated so far over portions of the 3D volume at different sizes.

Figure 8:
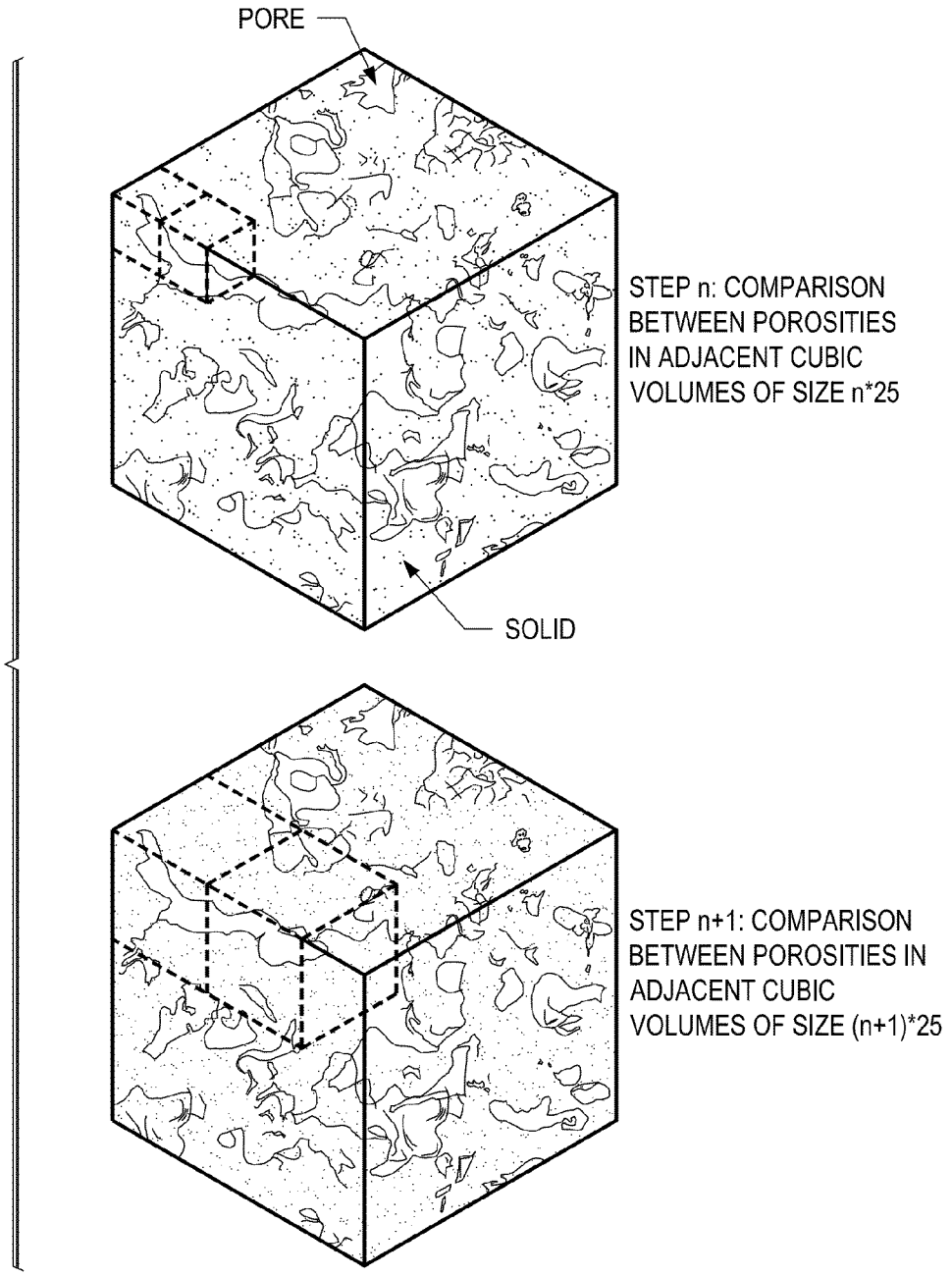
FIG. 8 is a diagram that illustrates one example of the selection of test volume sizes in sampling a 3D digital image volume, according to embodiments of the invention.

If additional test volume sizes are to be analyzed (decision 618 is "yes"), process 606 is repeated to select the next additional test volume size. Typically, the different test volume sizes are selected in order to determine the mean difference value over multiple different sized portions of the 3D digital volume. One approach to process 606 is to incrementally select the different test volume sizes to include either a greater number of voxels or fewer voxels. FIG. 8 illustrates one example of the selection of test volume sizes using increments of 25 voxels on a side. In this example, the first test volume size is 25 voxels on a side, the second test volume size is 50 voxels on a side, the third test volume size is 75 voxels on a side, and so on. In FIG. 8, size refers to the length in voxels of one side of the cubic volume.

Upon decision 618 determining that no additional test volume sizes remain to be analyzed (decision 618 is "no"), the testing tool may determine the REV for the porous medium currently being analyzed in process 620. In those embodiments in which decision 618 involves the determination of the REV in determining whether to analyze another test volume size, this process 620 will have been performed as part of that decision 618.

As will be described in further detail below, by calculating the difference values and the representative elementary volume, the testing tool and system can improve the efficiency of direct numerical simulation by determining an ideal size of a digital volume to analyze that minimizes the uncertainty in the material properties simulated due to heterogeneity within the input volume. As such, the testing system can determine a testing size that minimizes the uncertainty in the material property values without unduly increasing the size of a portion of the digital volume to analyze. Accordingly, the testing tool and system can improve both computational accuracy and computational efficiency.

Figure 9:
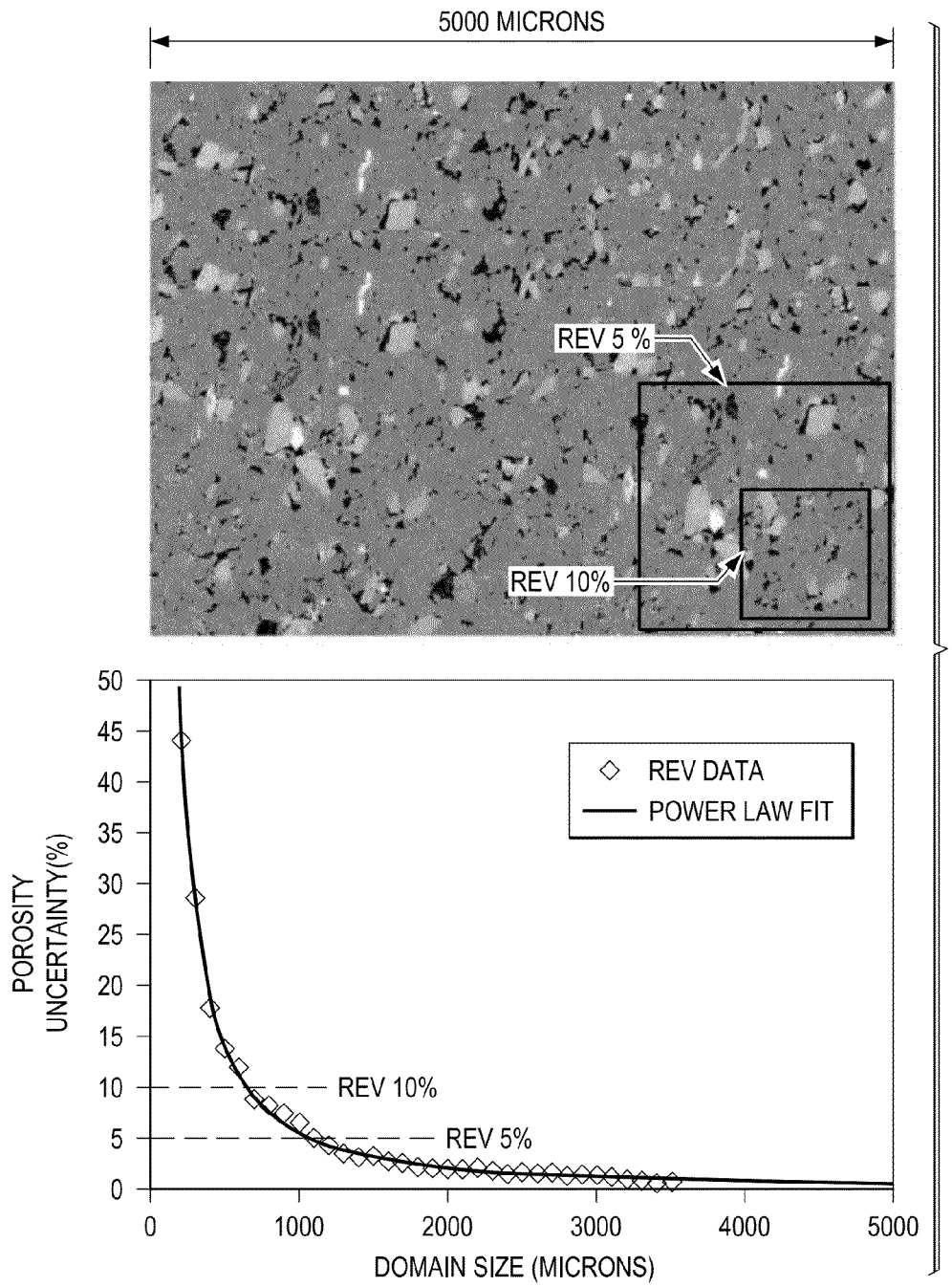
FIG. 9 is a diagram that illustrates an example of a rock sample and an example of a plot of the difference values, according to an embodiment of the invention.

In some embodiments of the invention, the representative elementary volume (REV) as determined for a rock sample in process 620 is a volume size for which a mean difference value p (or p %) of one or more calculated material property values between two adjacent portions of a digital volume of that size will differ by no more than a predetermined percentage difference value REV %. FIG. 9 illustrates an example of a rock sample and an example of a plot of the difference values as obtained by one of the embodiments described above. In the bottom pane of FIG. 9, uncertainty in calculated porosity value, as based on mean difference values (labeled as REV %), is plotted against domain sizes corresponding to the test volume sizes. This plot shows that the porosity uncertainty curve fits a power law characteristic over the test volume sizes, with arrows pointing to the domain sizes corresponding to the REV 10% and REV 5% volume sizes. A smaller REV % for a given test volume size indicates closer correspondence of the material property values calculated for the two adjacent portions of the 3D digital volume. The top pane of FIG. 9 illustrates an x-ray tomographic image domain of approximately 5000 microns for a rock sample, and the relative sizes of the test volume sizes for REV 5% (~1200 microns) and REV 10% (~800 microns) porosity uncertainty relative to that image domain.

Figure 10:
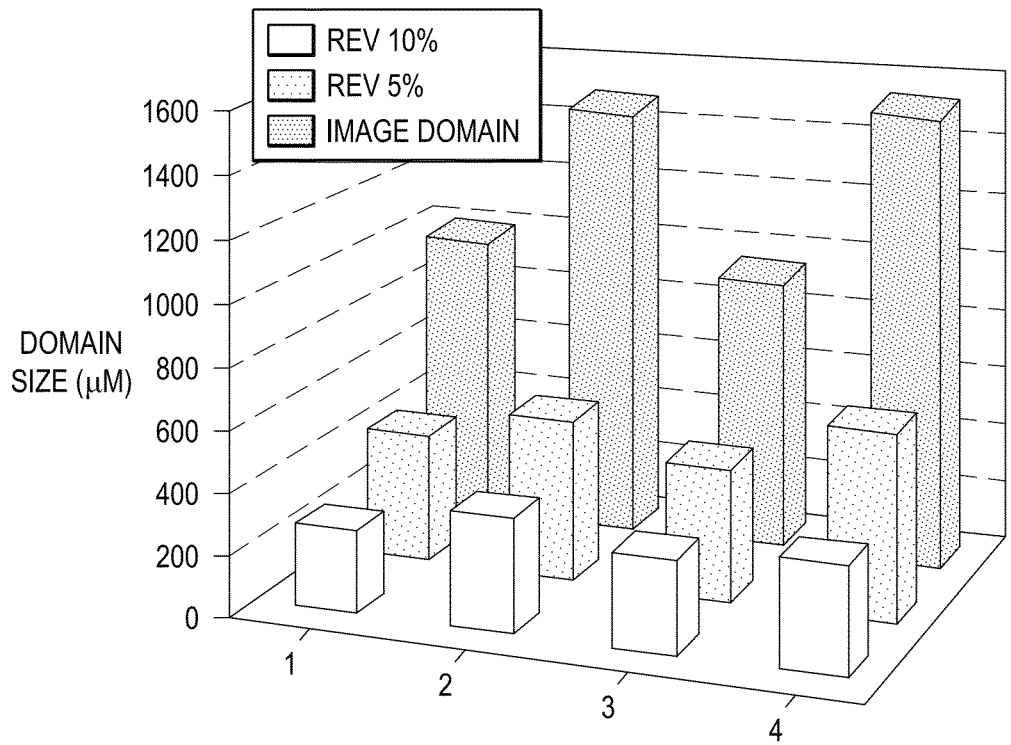
FIG. 10 is a diagram that illustrates an example of a study of REV % for porosity uncertainty for four different digital volumes, according to an embodiment of the invention.

The testing tool can define an REV to be used for subsequent direct numerical simulation measurements based on a tradeoff of a desired percentage difference value REV % between two adjacent sample volumes on one hand, and reducing the test volume size on the other hand, essentially balancing the REV % with the test volume size. FIG. 10 illustrates one study of REV % for porosity uncertainty for four different digital volumes. The image domain size is given by the solid bar, the mid gray bar shows the test volume size at 5% uncertainty in porosity for each image domain, and the light gray bar shows the test volume size at 10% porosity uncertainty for each image domain. The greater the difference in domain sizes between the digital image domain volume and the specified REV % test volume size, the greater the computational savings that are available by analyzing an REV test volume rather than the entire image domain, so long as the uncertainty of the REV % is tolerable. Of course, computation of the property value over the full domain will provide more certainty that the computed material property will not be affected by local heterogeneity within the digital volume.

According to embodiments of this invention, the testing tool can calculate the difference value p and difference value percentage p % in process 612 using:

$$p = 2 \cdot \text{abs}(V_A - V_B)/(V_A + V_B), \text{ and}$$

$$p\% = 100 \cdot p;$$

where $V_A, V_B$ are material property values calculated or simulated for the adjacent sample volumes. As described above, the testing tool computes the difference value p a number of times for each test volume size. From the set of difference values for each test volume size, the mean difference value or mean difference value as a percentage p % may be calculated in processes 615, 616 using:

$$\langle p \rangle = \frac{1}{n}\sum_{i=1}^{n} p_i; \text{ or}$$

$$\langle p\% \rangle = \frac{1}{n}\sum_{i=1}^{n} p\%_i$$

where n is the total number of times the difference value p (or percentage p %) has been computed for each test volume size and i refers to the index of difference value p (or percentage difference value p %) for a specific instance of two adjacent sample volumes at that test volume size. For the case of process 615 in which the testing tool utilizes a cumulative mean difference value p or percentage p %, after the difference value p (or difference value percentage p %) is computed for two adjacent sample volumes as given above, the mean difference value p (or mean difference value percentage p %) is calculated over that newly-calculated value in combination with the previous calculated values at that test volume size.

Figure 11:
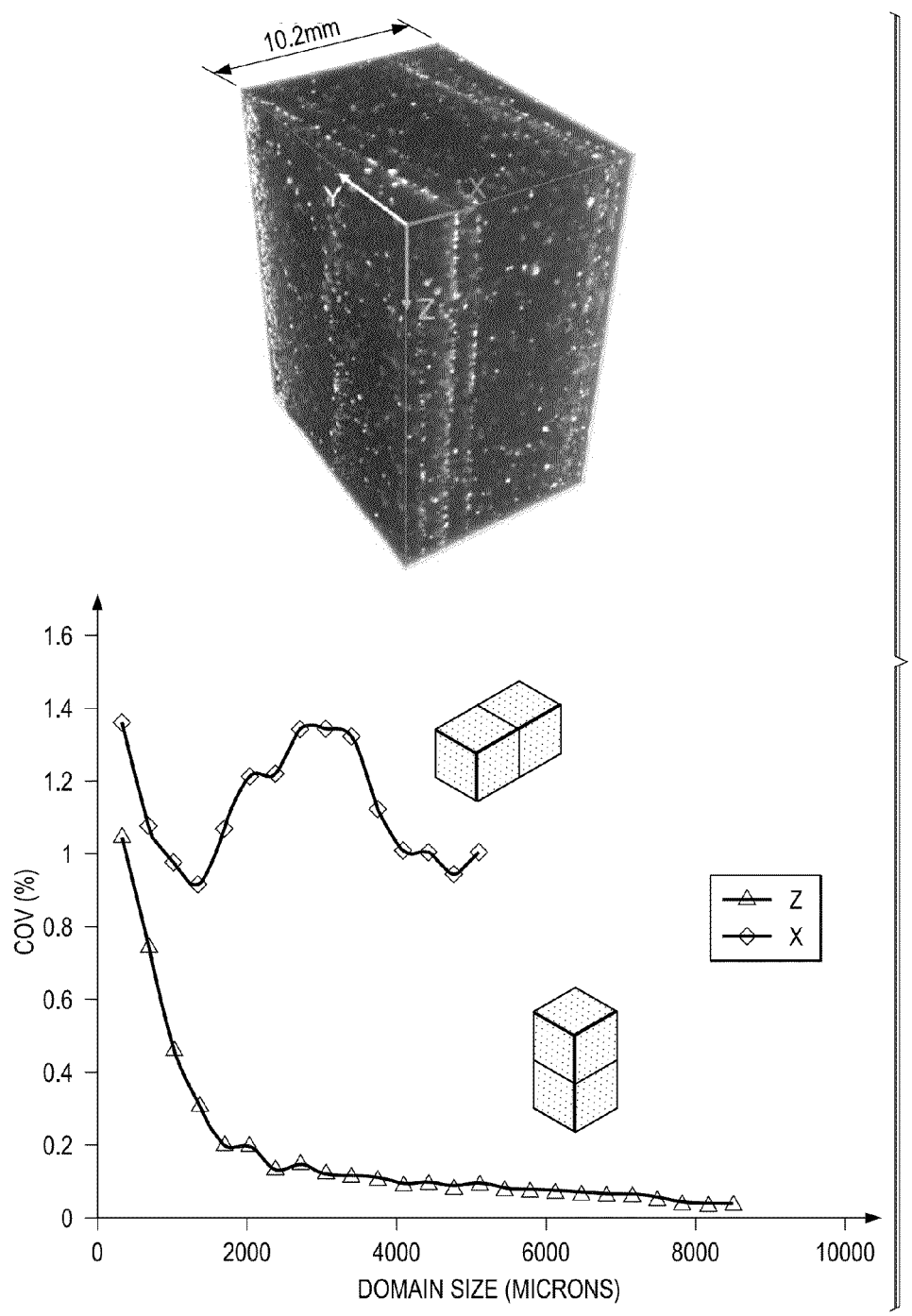
FIG. 11 is a diagram that illustrates an example of an x-ray tomographic image and an example of a plot to assess anisotropy, according to an embodiment of the invention.

According to alternative embodiments of the invention, the testing tool can be configured to analyze anisotropy within the digital volume by conducting the REV analysis in orthogonal directions. For example, the testing tool can be configured to conduct REV analysis by selecting adjacent test volumes aligned in the x-direction. The testing tool can then be configured to conduct REV analysis by selecting adjacent test volumes aligned in the z-direction. The testing tool can then compare the plots of the mean difference value percentage or the cumulative mean difference value percentage for each direction. If anisotropy is present within the volume, there is a difference in the shape of the mean (or cumulative mean) difference curves for each direction. FIG. 11 illustrates an example of an x-ray tomographic image along with a corresponding covariance plot in order to assess such anisotropy, according to an example implementation. The top pane of FIG. 11 shows an x-ray tomographic image volume that exhibits layering heterogeneity in the x-direction; this x-ray tomographic image has a resolution of 13.6 microns per voxel. The bottom pane of FIG. 11 shows the results of an implementation of the testing tool according to an implementation that assesses anisotropy, by way of a plot of coefficient of variation for probe directions along each of the x-axis and the z-axis. In this example, a covariance in grayscale values (COV) is computed, rather than a material property directly. Representative elementary volume analysis shows that porosity uncertainty in the z-direction decreases as volume size increases. However, porosity uncertainty in the x-direction is impacted by the heterogeneity in the sample, which is occurring on the length scale of sedimentary layering. While the covariance drops significantly with domain size along the z-direction, covariance varies with domain size along the x-direction in response to the layering heterogeneity. Comparison of these covariance characteristics demonstrates the presence of anisotropy within the image volume.

According to some embodiments, the testing tool can be configured to assess the REV % volume when larger scale heterogeneity is present in the digital volume. That is, in some circumstances the desired uncertainty in terms of REV % for a certain material property can have a domain size which is greater than that of the entire digital image volume itself. In this case, the testing tool can compute an REV % by fitting a power law to the mean difference data plot obtained from the finite image volume, and extrapolating the result to larger domain sizes. For example, in the right-hand pane of FIG. 9, the power law fit can extend beyond the actual REV data as shown by a dotted line, projecting the porosity uncertainty to domain sizes beyond the 5000 microns of the image volume itself.

Figure 12:
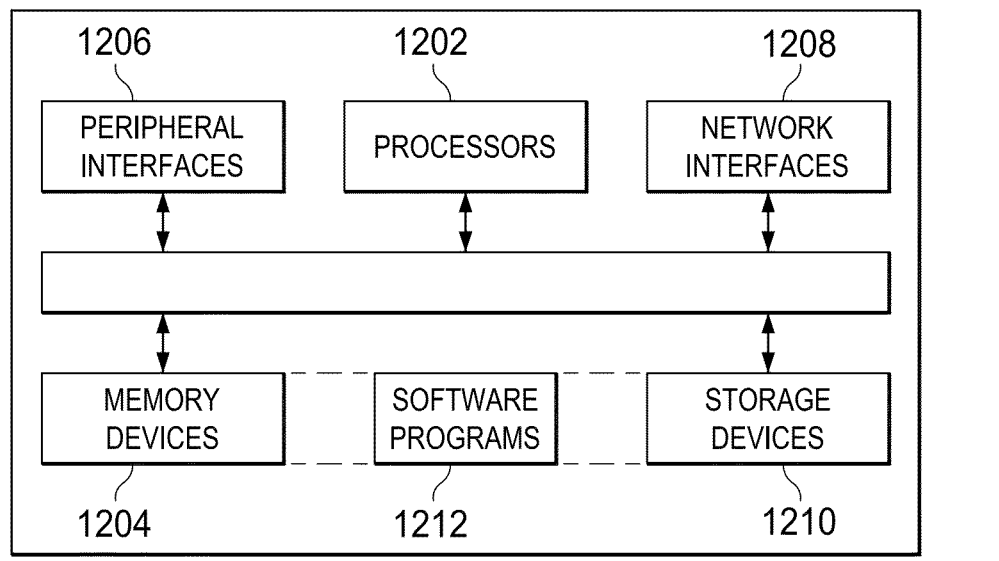
FIG. 12 is a generic block diagram that illustrates components of a computing device, according to an embodiment of the invention.

FIG. 12 illustrates an example of a hardware configuration for a computing device 1200 that implements the testing tool for performing one or more of the processes described above, according to embodiments of the invention. While FIG. 12 illustrates various components contained in an example of the architecture of computing device 1200, it is to be understood that this architecture is presented in a generic fashion, with the particular architecture and arrangement depending on particular implementations. As such, it is to be appreciated that additional components can be added, existing components can be removed, and alternative components can replace, those components illustrated in the example of FIG. 12.

As illustrated in FIG. 12, the computing device 1200 includes one or more processors 1202 of any one of a number of core configurations, operating at corresponding clock frequencies. In this example, computing device 1200 also includes one or more memory devices 1204 serving as a main memory during the operation of the computing device 1200, for example as data memory. In this example, computing device 1200 also includes one or more peripheral interfaces 1206, such as keyboards, mice, touchpads, computer screens, touchscreens, etc., for enabling human interaction with and manipulation of the computing device 1200.

Computing device 1200 also includes one or more network interfaces 1208 for communicating via one or more networks, such as Ethernet adapters, wireless transceivers, or serial network components, for communicating over wired or wireless media using protocols. In this regard, computing device 1200 can reside on a network, such that the computational tasks described above in connection with FIGS. 6a and 6b may be carried out in a distributed manner, for example utilizing data or program instructions stored on other computing resources available to computing device 1200 over such a network connection. Computing device 1200 also includes one or more storage devices 1210 of varying physical dimensions and storage capacities, such as flash drives, hard drives, random access memory, etc., for storing data, such as images, files, and program instructions for execution by the one or more processors 1202.

Whether in memory devices 1204 or storage devices 1210, computing device 1200 includes one or more software programs 1212 containing program instructions that, when executed by processors 1202, cause computing device 1200 and other associated hardware to operate as the testing tool referred to above in connection with the described embodiments of the invention by performing the processes described herein. Copies of these one or more software programs 1212 can be stored in the one or more memory devices 1204, in the one or more storage devices 1210, or both, or may otherwise be available to computing device 1200 via network interfaces 1208. Likewise, the data utilized by one or more software programs 1212 can be stored in the one or more memory devices 1204 and/or in the one or more storage devices 1210, or may otherwise be available to computing device 1200 via network interfaces 1208.

In embodiments of this invention, the components of the computing device 1200 as described above need not be enclosed within a single enclosure or even located in close proximity to one another. Those skilled in the art will appreciate that the above-described architecture and components are provided by way of an example only, as the computing device 1200 can include any type of hardware, firmware, or software for performing the disclosed functions. Computing device 1200 can also be implemented in part or in whole by electronic circuit components or processors, such as application-specific integrated circuits (ASICs) or field-programmable gate arrays (FPGAs).

While this invention has been described with reference to examples of its embodiments, it is contemplated that those skilled in the art having reference to this specification will be readily able to make various modifications to the described implementations without departing from the true spirit and scope. The terms and descriptions used herein are set forth by way of illustration only and are not meant as limitations. In particular, although the method has been described by examples, the steps of the method may be performed in a different order than illustrated or simultaneously. Furthermore, to the extent that the terms "including", "includes", "having", "has", "with", or variants thereof are used in either the detailed description and the claims, such terms are intended to be inclusive in a manner similar to the term "comprising." As used herein, the terms "one or more of" and "at least one of" with respect to a listing of items such as, for example, A and B, means A alone, B alone, or A and B. Further, unless specified otherwise, the term "set" should be interpreted as "one or more." Those skilled in the art will recognize that these and other variations are possible within the spirit and scope as defined in the following claims and their equivalents.

What is claimed is:

1. A method for determining, from a sample of a material, a representative elementary volume (REV) of the material based on one or more material properties, the method comprising:
   defining a plurality of test volume sizes;
   determining, for each of the plurality of test volume sizes, a difference value of a material property between sample volumes of one or more pairs of adjacent sample volumes from a three-dimensional (3D) digital volume representative of the sample of material, each sample volume of a size at that test volume size; and
   identifying the REV for the 3D digital volume from the difference values determined at each of the plurality of test volume sizes.

2. The method of claim 1, wherein each test volume size corresponds to a number of voxels;
   and wherein the step of determining the difference value for each of the plurality of test volumes comprises:
     selecting a first pair of sample volumes from the 3D digital volume, the first pair comprising first and second sample volumes adjacent to one another within the 3D digital volume and each containing the number of voxels of the test volume size;
     operating a computer to calculate a material property value for each of the first and second sample volumes; and calculating a difference value between the material property values of the first and second sample volumes.

3. The method of claim 2, wherein the step of calculating the difference value comprises evaluating an equation corresponding to:

$$p = 2 \times \frac{|V_A - V_B|}{V_A + V_B}$$

where p is the difference value, $V_A$ is the material property value for the first sample volume, and $V_B$ is the material property value for the second sample volume.

4. The method of claim 2, wherein the step of determining the difference value for each of the plurality of test volume sizes further comprises:
repeating the selecting, operating, and calculating steps for a selected number of instances; and
then calculating a mean of the calculated difference values for the test volume size.

5. The method of claim 2, wherein the step of determining the difference values for each of the plurality of test volumes further comprises:
repeating the selecting, operating, and calculating steps;
then calculating a cumulative mean of the calculated difference values for the test volume size;
evaluating the cumulative mean relative to a convergence criterion; and
responsive to the cumulative mean not satisfying the convergence criterion, repeating the selecting and calculating steps, the step of then calculating a cumulative mean, and the evaluating step.

6. The method of claim 2, wherein the first and second sample volumes are adjacent to one another in a first direction so that the difference value corresponds to a difference value for the first direction;
wherein the step of determining the difference value for each of the plurality of test volumes further comprises:
selecting a second pair of sample volumes from the 3D digital volume, comprising third and fourth sample volumes adjacent to one another within the 3D digital volume in a second direction orthogonal to the first direction, each of the third and fourth sample volumes containing the number of voxels of the test volume size;
calculating the material property value for each of the third and fourth sample volumes; and
calculating a difference value for the second direction between the material property values for the third and fourth sample volumes;
and further comprising:
determining anisotropy of the material sample by comparing the difference values for the first and second directions.

7. The method of claim 2, wherein the step of operating a computer to calculate a material property comprises operating the computer to perform direct numerical simulation using a technique selected from the group consisting of lattice Boltzmann, finite difference, finite element, and random walk.

8. The method of claim 1, further comprising:
acquiring the 3D digital volume, in the form of a 3D image volume of the material sample, utilizing one of x-ray tomography, micro x-ray tomography, nano x-ray tomography, focused ion beam scanning electron microscopy, nuclear magnetic resonance, or neutron tomography.

9. The method of claim 8, wherein the material sample comprises one of whole core, side wall cores, outcrops, drill cuttings, laboratory generated synthetic rock samples, sand packs, and cemented packs.

10. The method of claim 8, wherein the acquiring step further comprises:
processing the 3D image volume using one or both of image enhancement techniques and segmentation techniques to produce the 3D digital volume in the form of a 3D derivative volume.

11. The method of claim 1, further comprising:
generating a 3D constructed volume using numerical algorithms or simulation methods to produce the 3D digital volume.

12. The method of claim 1, wherein the step of identifying the REV comprises:
selecting, as the REV, a volume corresponding to a test volume size having a difference value corresponding to a desired uncertainty level for a material property.

13. The method of claim 12, wherein the difference value corresponding to the desired uncertainty level is the mean difference level of the test volume size.

14. The method of claim 1, wherein the step of identifying the REV comprises:
identifying a relationship of the difference values determined at each of the plurality of test volume sizes to test volume size;
from the identified relationship, selecting an REV as a volume corresponding to a desired uncertainty level for a first material property.

15. The method of claim 14, wherein the selected REV is a volume larger than the largest one of the plurality of test volume sizes.

16. A non-transitory computer readable storage medium storing program instructions that, when executed by one or more processors, cause the one or more processors to determine, from a sample of a material, a representative elementary volume (REV) of the material based on one or more material properties, by performing a plurality of operations comprising:
defining a plurality of test volume sizes, each corresponding to a number of voxels;
determining, for each of the plurality of test volume sizes, a difference value of a material property between sample volumes of one or more pairs of adjacent sample volumes within a three-dimensional (3D) digital volume representative of a material sample, each sample volume having the number of voxels associated with that test volume size; and
identifying the REV for the 3D digital volume from the difference values for determined at each of the plurality of test volume sizes.

17. The computer readable storage medium of claim 16, wherein the operation of determining the difference value for each of the plurality of test volumes comprises:
selecting a first pair of sample volumes from the 3D digital volume, the first pair comprising first and second sample volumes adjacent to one another within the 3D digital volume;
calculating a material property value for each of the first and second sample volumes; and
calculating a difference value between the material property values of the first and second sample volumes.

18. The computer readable storage medium of claim 17, wherein the operation of calculating the difference value comprises evaluating an equation corresponding to:

$$p = 2 \times \frac{|V_A - V_B|}{V_A + V_B}$$

where p is the difference value, $V_A$ is the material property value for the first sample volume, and $V_B$ is the material property value for the second sample volume.

19. The computer readable storage medium of claim 17, wherein the operation of determining the difference value for each of the plurality of test volumes further comprises:
repeating the selecting and calculating operations for a selected number of instances; and
then calculating a mean of the calculated difference values for the test volume size.

20. The computer readable storage medium of claim 17, wherein the operation of determining the difference values for each of the plurality of test volumes further comprises:
repeating the selecting and calculating operations;
then calculating a cumulative mean of the calculated difference values for the test volume size;
evaluating the cumulative mean relative to a convergence criterion; and
responsive to the cumulative mean not satisfying the convergence criterion, repeating the selecting and calculating operations, the operation of then calculating a cumulative mean, and the evaluating operation.

21. The computer readable storage medium of claim 17, wherein the first and second sample volumes are adjacent to one another in a first direction so that the difference value corresponds to a difference value for the first direction;
wherein the operation of determining the difference value for each of the plurality of test volumes further comprises:
selecting a second pair of sample volumes from the 3D digital volume, comprising third and fourth sample volumes adjacent to one another within the 3D digital volume in a second direction orthogonal to the first direction, each of the third and fourth sample volumes containing the number of voxels of the test volume size;
calculating the material property value for each of the third and fourth sample volumes; and
calculating a difference value for the second direction between the material property values for the third and fourth sample volumes;
and further comprising:
determining anisotropy of the material sample by comparing the difference values for the first and second directions.

22. The computer readable storage medium of claim 16, wherein the operation of identifying the REV comprises:
selecting, as the REV, a volume corresponding to a test volume size having a difference value corresponding to a desired uncertainty level for a material property.

23. The computer readable storage medium of claim 16, wherein the operation of identifying the REV comprises:
identifying a relationship of the difference values determined at each of the plurality of test volume sizes to test volume size;
from the identified relationship, selecting an REV as a volume corresponding to a desired uncertainty level for a first material property.

24. A system for analyzing material samples, the system comprising:
a scanner configured to produce a three dimensional (3D) digital volume, wherein the 3D digital volume is a representation of a material sample; and
a computing device coupled to the scanner and comprising:
one or more processors; and
one or more memory devices, coupled to the one or more processors, storing program instructions that, when executed by the one or more processors, cause the one or more processors to determine, from a sample of a material, a representative elementary volume (REV) of the material based on one or more material properties, by performing a plurality of operations comprising:
defining a plurality of test volume sizes, each corresponding to a number of voxels;
determining, for each of the plurality of test volume sizes, a difference value of a material property between sample volumes of one or more pairs of adjacent sample volumes within a three-dimensional (3D) digital volume representative of a material sample, each sample volume having the number of voxels associated with that test volume size; and
identifying the REV for the 3D digital volume from the difference values for determined at each of the plurality of test volume sizes.

25. The system of claim 24, wherein the operation of determining the difference value for each of the plurality of test volumes comprises:
selecting a first pair of sample volumes from the 3D digital volume, the first pair comprising first and second sample volumes adjacent to one another within the 3D digital volume;
calculating a material property value for each of the first and second sample volumes; and
calculating a difference value between the material property values of the first and second sample volumes.

26. The system of claim 25, wherein the difference value is calculated using an equation comprising:

$$p = 2 \times \frac{|V_A - V_B|}{V_A + V_B}$$

where p is the difference value, $V_A$ is the first material property value, and $V_B$ is the second material property value.

27. The system of claim 25, wherein the operation of determining the difference value for each of the plurality of test volumes further comprises:
repeating the selecting and calculating operations for a selected number of instances; and
then calculating a mean of the calculated difference values for the test volume size.

28. The system of claim 25, wherein the operation of determining the difference values for each of the plurality of test volumes further comprises:
repeating the selecting and calculating operations;
then calculating a cumulative mean of the calculated difference values for the test volume size;
evaluating the cumulative mean relative to a convergence criterion; and
responsive to the cumulative mean not satisfying the convergence criterion, repeating the selecting and calculating operations, the operation of then calculating a cumulative mean, and the evaluating operation.

29. The system of claim 25, wherein the first and second sample volumes are adjacent to one another in a first direction so that the difference value corresponds to a difference value for the first direction;
   wherein the operation of determining the difference value for each of the plurality of test volumes further comprises:
      selecting a second pair of sample volumes from the 3D digital volume, comprising third and fourth sample volumes adjacent to one another within the 3D digital volume in a second direction orthogonal to the first direction, each of the third and fourth sample volumes containing the number of voxels of the test volume size;
      calculating the material property value for each of the third and fourth sample volumes; and
      calculating a difference value for the second direction between the material property values for the third and fourth sample volumes;
   and further comprising:
      determining anisotropy of the material sample by comparing the difference values for the first and second directions.

30. The system of claim 24, wherein the operation of identifying the REV comprises:
   selecting, as the REV, a volume corresponding to a test volume size having a difference value corresponding to a desired uncertainty level for a material property.

31. The system of claim 24, wherein the operation of identifying the REV comprises:
   identifying a relationship of the difference values determined at each of the plurality of test volume sizes to test volume size;
   from the identified relationship, selecting an REV as a volume corresponding to a desired uncertainty level for a first material property.

* * * * *